United States Defensive Publication [19] (H) [11] T100,404

Wu [43] Mar. 3, 1981

[54] RUMEN-STABLE PELLET COATINGS

[76] Inventor: Stephen H. W. Wu, 1104 Meadow La., Kingsport, Tenn. 37663

[21] Appl. No.: 125,829

[22] Filed: Feb. 29, 1980

[51] Int. Cl.[3] ..... A61K 31/30; A61K 31/32; A61K 31/56; A61K 31/58

[52] U.S. Cl. ..... 424/32; 424/31

[57] ABSTRACT

Pellets are disclosed which are adapted for oral administration to a ruminant, the pellets having a core material beneficial to ruminants postruminally, and a coating surrounding the core material which protects the core material in the rumen and releases it in the abomasum, said coating having an outer layer consisting essentially of a blend of about 55–75 parts by weight of a film-forming polymeric material containing at least one basic amino grouping and in which the nitrogen content is from 3 to 14% by weight of the total molecular weight of the polymeric material, e.g., cellulose propionate morpholinobutyrate, and about 45–25 parts by weight of a hydrophobic material such as aluminum oleate, and an inner layer consisting essentially of a blend of about 45–55 parts by weight of a film-forming polymeric material containing at least one basic amino grouping and in which the nitrogen content is from 3 to 14% by weight of the total molecular weight of the polymeric material, e.g., cellulose propionate morpholinobutyrate, and about 55–45 parts by weight of a hydrophobic material, said coating making up about 5 to about 50% of the weight of said pellet.

6 Claims, No Sheets Drawing,

11 Pages Specification

The file of this unexamined application may be inspected and copies thereof may be purchased (849 O.G. 1221, Apr. 9, 1968).